United States Patent [19]

Pellico

[11] Patent Number: 4,770,634
[45] Date of Patent: Sep. 13, 1988

[54] METHOD FOR TREATING TEETH WITH FOAMABLE FLUORIDE COMPOSITIONS

[76] Inventor: Michael A. Pellico, 3024 Military Ave., Los Angeles, Calif. 90272

[21] Appl. No.: 872,851

[22] Filed: Jun. 11, 1986

[51] Int. Cl.$^4$ .............................................. A61K 7/18
[52] U.S. Cl. ................... 433/217.1; 433/215; 424/45; 424/52
[58] Field of Search ............... 424/45, 49, 52; 433/215, 217.1; 106/35

[56] References Cited

U.S. PATENT DOCUMENTS

| | | | |
|---|---|---|---|
| 3,527,219 | 9/1970 | Greenberg | 128/260 |
| 4,137,303 | 1/1979 | Gaffar et al. | 424/52 |
| 4,138,814 | 2/1979 | Weitzman | 433/215 |
| 4,522,806 | 6/1985 | Muhlemann et al. | 424/52 |
| 4,601,898 | 7/1986 | Stier et al. | 424/52 |

Primary Examiner—Joseph L. Schofer
Assistant Examiner—A. Fugo
Attorney, Agent, or Firm—Donald Diamond

[57] ABSTRACT

A foamable fluoride composition, for use in dental therapy, is provided that contains water, dental fluoride, foaming agent, foam-wall thickener and acidifying agent. An illustrative composition comprises water, sodium fluoride, sucrose distearate, glycerol and phosphoric acid. The foamable fluoride composition, which is packaged in an aerosol container in combination with an aerosol propellant, is dispensed into the trough of a dental tray as a dense, stable, non-flowable foam which is superimposed about and into engagement with the teeth to be treated to thereby effect fluoride uptake by the dental enamel. The fluoride foam provides substantially the same fluoride uptake as a fluoride gel but this result is achieved by the fluoride foam with substantially less fluoride in the tray than that which is present in a corresponding tray containing a like volume of fluoride gel.

9 Claims, No Drawings

METHOD FOR TREATING TEETH WITH FOAMABLE FLUORIDE COMPOSITIONS

BACKGROUND OF THE INVENTION

This invention relates to dental compositions and, more particularly, to foamable fluoride compositions which are adapted to provide stable foams for use in dental therapy.

It is generally understood in the dental art that certain kinds of food decay are initiated by acid etching of the tooth enamel with the source of the acid being a metabolite resulting from bacterial and enzymatic action on food particles in the oral cavity. It is generally accepted that plaque—which is a soft accumulation on the tooth surfaces consisting of an organized structure of microorganisms, proteinaceous and carbohydrate substances, epithelial cells, and food debris—is a contributory factor in the development of various pathological conditions of the teeth and soft tissue of the oral cavity. It has been suggested that the saccharolytic organisms of the oral cavity, which are associated with the plaque, cause decalcification beneath the plaque matrix through metabolic activity which results in the accumulation and localized concentration of organic acids. The etching and decalcification of the enamel may continue until the pulp chamber of the tooth is reached.

Fluoride compounds have been incorporated into dental topicals and into consumables to provide an orally beneficial effect by reducing the dissolving action of acids on dental enamel. It has been reported that the fluoride combines with hydroxyapatite, the crystalline structure of the teeth, to produce a modified crystalline structure which is more resistant to acid attack.

Diverse fluoride compounds have been disclosed in the prior art for use in dental care including, for example, sodium fluoride, sodium monofluorophosphate, stannous fluoride, fluoroalkyl phosphates, and quaternary ammonium fluorides.

The fluorides can be incorporated into gels, rinses, toothpaste, tooth powder, chewing gum and the like for topical application. Fluoride treatment can also be undertaken through consumables such as fluoridated drinking water and fluoride tablets. Heretofore, fluoride gels have been used in dental practice to topically apply fluoride to the teeth. The fluoride gel is usually supplied as a thick gel in a plastic bottle from which it is dispensed into the trough of a plastic dental tray that is inserted into the mouth in juxtaposition to the teeth whereby the teeth engage the gel for about 1 to 4 minutes, as per the supplier's instructions.

A typical fluoride gel contains water, a water soluble dental fluoride such as sodium fluoride, glycerol, an acidifying agent such as phosphoric acid, and a water soluble thickener such as carboxymethyl cellulose, polyvinyl alcohol, or xanthan gum.

An illustrative fluoride gel formulation is as follows:

| INGREDIENTS | PARTS BY WEIGHT |
|---|---|
| Water | 85.5 |
| Sodium fluoride | 2.7* |
| Xanthan gum | 3.2 |
| Glycerol | 3.4 |
| Phosphoric acid (85%) | 4.1 |

*Available fluoride 1.2 pts. by wt.

The water soluble thickener is selected so as to provide a highly viscous and thick system for maintaining the gel in the tray and in positive contact with the teeth, since a thin gel would tend to flow away from the tooth surface and thereby reduce fluoride uptake by the tooth and, additionally, a thin gel could flow out of the tray and cause the patient to gag and choke.

The acidifying agent is selected so as to provide the fluoride gel with a pH between about 3.0 and 4.5 which facilitates and enhances fluoride uptake by the teeth.

There are several problems associated with the use of fluoride gels in dental therapy. One of the most vexing problems is that of viscosity. The fluoride gel must be thick enough so that it does not flow out of the dental tray while the tray is in the patient's mouth and, at the same time the gel must be thin enough to be dispensed from a plastic bottle into the tray in preparation for the fluoride treatment. Because it is extremely difficult to formulate a fluoride gel that flows from a plastic dispensing bottle and yet remains stationary in the dental tray for up to 4 minutes while in the mouth, the fluoride gels heretofore available had a tendency to flow while in the tray and cause patient gagging during the course of treatment.

Another problem associated with fluoride gels is that of toxicity. Fluorides have a low concentration threshold for exerting toxic effects. It is reported that severe symptoms can be manifested from the ingestion of less than one gram of sodium fluoride. Thus, the ingestion of any significant amount of fluoride gel can produce serious consequences. This risk is especially noteworthy because fluoride gels, which have been flavored to mask the acidic taste, are most often used to treat children and the flavoring can increase the chance of unintentionally swallowing a significant amount of the semi-fluid gel.

A further problem associated with fluoride gels is the cost-effectiveness of the thick gel. In view of the high viscosity of the fluoride gels, the only fluoride which is available for uptake by the tooth is that which is in the immediate vicinity of the tooth surface. The remaining fluoride, which is the bulk of the fluoride in the tray, is unavailable for dental uptake because fluoride movement is restricted by the high viscosity of the gel.

Accordingly, it would be advantageous to provide a tray-fluoride that is non-flowable and which requires substantially less fluoride in the tray to achieve the same fluoride uptake as a corresponding volume of fluoride gel.

SUMMARY OF THE INVENTION

In accordance with one aspect of this invention, there is provided a foamable fluoride composition comprising:
 (a) a water soluble dental fluoride in an amount to provide the composition with about 0.5 to about 5 wt. % available fluoride;
 (b) an orally compatible and acid stable foaming agent in an amount from about 4 to about 20 wt. %;
 (c) an orally compatible and acid stable foam-wall thickener in an amount from about 2 to about 20 wt. %;
 (d) an orally compatible acidifying agent in an amount to provide the composition with a pH from about 3.0 to about 4.5; and
 (e) water to 100 wt. %.

In accordance with a second aspect of this invention, there is provided a method for treating teeth with a fluoride foam, which comprises:

(a) dispensing a pressurized and foamable fluoride composition from an aerosol container into the trough of a dental tray to form a fluoride foam within the trough, wherein the foamable fluoride composition contains: a water soluble dental fluoride in an amount to provide the composition with about 0.5 to about 5 wt. % available fluoride; an orally compatible and acid stable foaming agent in an amount from about 4 to about 20 wt. %; an orally compatible and acid stable foam-wall thickener in an amount from about 2 to about 20 wt. %; an orally compatible acidifying agent in an amount to provide the composition with a pH from about 3.0 to about 4.5; and water to 100 wt. %; and (b) superimposing the trough of the dental tray and its fluoride foam content about and into engagement with the teeth to be treated to effect fluoride uptake by such teeth.

DETAILED DESCRIPTION

The foamable fluoride compositions of this invention comprise aqueous solutions containing water soluble dental fluoride, foaming agent, foam-wall thickener, and acidifying agent.

Illustrative water soluble dental fluorides which can be used in the practice of this invention include sodium fluoride, sodium monofluorophosphate, stannous fluoride, fluoroalkyl phosphate salts as described in U.S. Pat. No. 2,955,985 (Kuna, 1960) such as monammonium 1,1,7-trihydroperfluoroheptyl phosphate, quaternary ammonium fluorides as described in U.S. Pat. No. 3,124,512 (Schmidt et al., 1964) such as doceyltrimethyl-ammonium fluoride, and mixtures thereof. The dental fluoride is generally present in the foamable fluoride composition in an amount to provide the composition with about 0.5 to about 5 wt. % available fluoride and, preferably, in an amount to provide the composition with about 1.0 to about 2.5 wt. % available fluoride. Sodium fluoride is particularly well suited for use in fluoride foam therapy and, when so used, is generally present in the foamable fluoride composition in an amount from about 1.1 to about 11.1 wt. % and, preferably in an amount from about 2.2 to about 5.6 wt. %.

Foaming agents which can be used in the practice of this invention to produce dense, stable, non-flowable foams are those which are orally compatible and acid stable and include, for example, sucrose monostearate, sucrose distearate, sodium lauryl sulfate and mixtures thereof. The foaming agent is generally present in the foamable fluoride composition in an amount from about 4 to about 20 wt. % and, preferably, in an amount from about 7 to about 13 wt. %.

Foam-wall thickeners which can be used in the practice of this invention to produce foams having enhanced stability are those which are orally compatible and acid stable and include for example, glycerol, sorbitol, hydrogenated starch hydrolysate (a polyol) available under the trademark Hystar TPF from Lonza, Inc., Fair Lawn, N.J. 07410 as a 70% solution, and mixtures thereof. The foam-wall thickener is generally present in the foamable fluoride composition in an amount from about 2 to about 20 wt. % and, preferably, in an amount from about 4 to about 15 wt. %.

Acidifying agents which can be used in the practice of this invention to facilitate and enhance fluoride uptake by the tooth structure from the fluoride foam are those which are orally compatible and include, for example, phosphoric acid, citric acid and mixtures thereof. The acidifying agent is generally present in the foamable fluoride composition in an amount to provide the aqueous solution with a pH from about 3.0 to about 4.5.

The foamable fluoride compositions are prepared by blending dental fluoride, foaming agent, foam-wall thickener and acidifying agent with water under mild mixing conditions at ambient temperature. The resulting aqueous solution is added in a predetermined amount to an open-mouth aerosol container. An appropriate aerosol valve is fitted over the mouth cf and secured to the container. The container is then charged through the aerosol valve with an aerosol propellant, such as propane, isobutane or a mixture thereof as, for example, a mixture of 4% propane and 96% isobutane, to an operating pressure of about 40 pounds per square inch gage. A dispensing actuator and spout assembly is then fitted onto the valve.

In use, the aerosol container, with its pressurized and foamable fluoride composition, is shaken and rotated to align the dispensing spout with the trough of a dental tray and the actuator is pressed to dispense an amount of flouride foam that substantially fills the volume defined by the trough. The tray is then placed in a patient's mouth so as to superimpose the trough and its fluoride foam content about and into engagement with the teeth to be treated. The fluoride foam, which is dense, stable and non-flowable, is maintained in engagement with the teeth for about 1 to 4 minutes to effect fluoride uptake by the teeth.

EXAMPLE I

The following examples illustrate various ingredients and concentrations which can be used in the preparation of the foamable fluoride compositions of this invention.

| 1(a) | |
|---|---|
| INGREDIENTS | PARTS BY WEIGHT |
| Water | 85.5 |
| Sodium fluoride | 2.7* |
| Sucrose distearate | 4.2 |
| Glycerol | 2.4 |
| Phosphoric acid (85%) | 4.1 |
| Flavor | q.s. |

*Available fluoride 1.2 pts. by wt.

The above formulation produces a dense foam which lasts over 10 minutes.

| 1(b) | |
|---|---|
| INGREDIENTS | PARTS BY WEIGHT |
| Water | 83.1 |
| Sodium fluoride | 3.1* |
| Sucrose distearate | 6.4 |
| Glycerol | 2.0 |
| Phosphoric acid (85%) | 4.1 |
| Flavor | q.s. |

*Available fluoride 1.4 pts. by wt.

The above formulation produces a very dense foam.

| 1(c) | |
|---|---|
| INGREDIENTS | PARTS BY WEIGHT |
| Water | 85.0 |
| Sodium fluoride | 3.1 |

1(c)

| INGREDIENTS | PARTS BY WEIGHT |
| --- | --- |
| Sucrose distearate | 4.0 |
| Glycerol | 2.2 |
| Phosphoric acid (85%) | 5.0 |
| Flavor | q.s. |

The above formulation has a pH of about 3.0 and produces a foam having excellent density and stability characteristics.

1(d)

| INGREDIENTS | PARTS BY WEIGHT |
| --- | --- |
| Water | 79.0 |
| Sodium fluoride | 3.1 |
| Sucrose monostearate | 10.1 |
| Glycerol | 2.2 |
| Phosphoric acid (85%) | 4.8 |
| Flavor | q.s. |

The above formulation produces a foam which is lighter than the foam produced by Examples 1(a) through 1(c).

1(e)

| INGREDIENTS | PARTS BY WEIGHT |
| --- | --- |
| Water | 85.0 |
| Sodium fluoride | 3.1 |
| Sodium lauryl sulfate | 3.0 |
| Glycerol | 3.2 |
| Phosphoric acid (85%) | 5.0 |
| Flavor | q.s. |

The above formulation produces a dense foam but it does not last as long as the foams produced by Examples 1(a) through 1(c).

1(f)

This example illustrates a foamable fluoride formulation wherein the fluoride source is stannous fluoride.

| INGREDIENTS | PARTS BY WEIGHT |
| --- | --- |
| Water | 85.5 |
| Stannous fluoride | 5.0 |
| Sucrose monostearate | 3.0 |
| Glycerol | 3.1 |
| Phosphoric acid (85%) | 4.0 |
| Flavor | q.s. |

1(g)

This example illustrates a foamable fluoride formulation wherein the flouride source is quaternary ammonium fluoride.

| INGREDIENTS | PARTS BY WEIGHT |
| --- | --- |
| Water | 71.5 |
| Dodecyl-trimethyl-ammonium fluoride | 12.5 |
| Sucrose monostearate | 8.0 |
| Citric acid | 8.0 |
| Flavor | q.s. |

Example II

A comparative study was undertaken to evaluate fluoride uptake by dental enamel from (a) the fluoride foam of this invention, (b) a commercial fluoride gel for professional use available under the trademark Nupro APF Gel, and (c) deionized water.

The foamable fluoride precursor for the fluoride foam contained 3.1 wt. % sodium fluoride, 6.0 wt. % sucrose distearate, 2.0 wt. % glycerol, 4.0 wt. % phosphoric acid (85%), 1.0 wt. % cherry flavor and water to 100 wt. %. The fluoride precursor was added to an open-mouth aerosol container and the final aerosol dispensing package was completed and pressurized in a customary manner as hereinabove described.

The following procedure was employed in the comparative study:

1. Thirty-six (36) bovine teeth were selected and labial enamel specimens were prepared in the following manner:
   (a) smoothed with 100 grit sandpaper on a lapidary wheel;
   (b) smoothed with 600 grit sandpaper on a lapidary wheel;
   (c) etched for 30 seconds with 2N perchloric acid; and
   (d) polished with a ragwheel and flour of pumice-distilled and water slurry (3:2).

2. The specimens were divided into groups of twelve (12) and treated under the following conditions:
   (a) specimen and treatment compositions were preheated to 37° C.; and
   (b) specimens were treated by immersing each respective group in its assigned treatment composition for 4 minutes with gentle agitation.

3. The treatment medium for each specimen group was as follows:

| GROUP | SPECIMEN | TREATMENT |
| --- | --- | --- |
| 1 | 1–12 | Deionized water |
| 2 | 13–24 | Fluoride foam |
| 3 | 25–36 | Nupro APF Gel |

4. Following treatment, each specimen was immediately rinsed with distilled water.

5. The rinsed specimens were placed in 1N potassium hydroxide saturated with tribasic calcium phosphate and maintained overnight on a constant immersion wheel (6 specimens bottle) to remove loosely bound calcium fluoride.

6. Upon completion of the potassium hydroxide immersion step, the specimens were rinsed with distilled water, windowed and one (1) enamel layer was removed from each specimen by decalcification in 3 ml of 0.5 N perchloric acid for 5 seconds.

7. The resulting decalcification solution for each group was analyzed for fluoride and calcium using accepted methods which included fluoride ion electrode and atomic absorption spectrophotometry.

The results of the comparative study are set forth in the following table:

TABLE I

| GROUP | TREATMENT | FLUORIDE UPTAKE | |
| --- | --- | --- | --- |
| | | PPM | DEPTH |
| 1 | Deionized water | 374 ± 38 | 1.16 ± 0.12 |
| 2 | Fluoride foam | 4210 ± 332 | 0.80 ± 0.07 |
| 3 | Nupro APF Gel | 4333 ± 318 | 1.08 ± 0.14 |

The comparative study shows that the fluoride uptake from the fluoride foam and from the fluoride gel is substantially the same.

The weight ratio of fluoride gel to fluoride foam, on a like volume basis, is about 2.5 to 1. Accordingly, the weight of fluoride in a dental tray substantially filled with fluoride foam is somewhat less than one-half the weight of fluoride in a like tray substantially filled with fluoride gel, where the percent of fluoride in each system is substantially the same. Thus, the fluoride foam of this invention provides substantially the same fluoride uptake as fluoride gel but this result is achieved by the fluoride foam with significantly less fluoride in the tray which markedly reduces exposure to fluoride toxicity in fluoride-tray treatment.

In view of the foregoing description and examples, it will become apparent to those of ordinary skill in the art that equivalent modifications thereof may be made without departing from the spirit and scope of this invention.

That which is claimed is:

1. A method for treating teeth with a fluoride foam, which comprises:
    (a) dispensing a pressurized and foamable fluoride composition from an aerosol container into the trough of a dental tray to form a fluoride foam within said trough, said foamable flouride composition containing:
    a water soluble dental fluoride in an amount to provide the composition with about 0.5 to about 5 wt. % available fluoride;
    an orally compatible and acid stable foaming agent in amount from about 4 to about 20 wt. %;
    an orally compatible and acid stable foam-wall thickener in an amount from about 2 to about 20 wt. %;
    an orally compatible acidifying agent in an amount to provide the composition with a pH from about 3.0 to about 4.5; and
    water to 100 wt. %; and
    (b) superimposing the trough of the dental tray and its flouride foam content about and into engagement with the teeth to be treated to effect fluoride uptake by such teeth.

2. The method of claim 1 wherein the dental fluoride is a member selected from the group consisting of sodium fluoride, sodium monofluorophosphate, stannous fluoride, fluoroakyl phosphate salt, quaternary ammonium fluoride and mixtures thereof.

3. The method of claim 2 wherein the dental fluoride is sodium fluoride.

4. The method of claim 1 wherein the foaming agent is a member selected from the group consisting of sodium lauryl sulfate, sucrose monostearate sucrose distearate and mixtures thereof.

5. The method of claim 1 wherein the foam-wall thickener is a member selected from the group consisting of glycerol, sorbitol, hydrogenated starch hydrolysate and mixtures thereof.

6. The method of claim 5 wherein the foam-wall thickener is glycerol.

7. The method of claim 1 wherein the acidifying agent is a member selected from the group consisting of phosphoric acid, citric acid and mixtures thereof.

8. The method of claim 7 wherein the acidifying agent is phosphoric acid.

9. The method of claim 1 wherein the dental fluoride is sodium fluoride in an amount from about 2.2 to about 5.6 wt. %, the foaming agent is sucrose distearate in amount from about 7 to about 13 wt. %, the foam-wall thickener is glycerol in an amount from about 4 to about 15 wt. %, and the acidifying agent is phosphoric acid.

* * * * *